US012633210B2

(12) United States Patent
Saito

(10) Patent No.: US 12,633,210 B2
(45) Date of Patent: May 19, 2026

(54) COMMUNICATION CONTROL APPARATUS, OPERATION TERMINAL, AND EQUIPMENT OPERATION SYSTEM

(71) Applicant: NEC Corporation, Tokyo (JP)

(72) Inventor: Yasuji Saito, Tokyo (JP)

(73) Assignee: NEC CORPORATION, Tokyo (JP)

( * ) Notice: Subject to any disclaimer, the term of this patent is extended or adjusted under 35 U.S.C. 154(b) by 66 days.

(21) Appl. No.: 18/027,025

(22) PCT Filed: Sep. 29, 2020

(86) PCT No.: PCT/JP2020/036777
§ 371 (c)(1),
(2) Date: Mar. 17, 2023

(87) PCT Pub. No.: WO2022/070233
PCT Pub. Date: Apr. 7, 2022

(65) Prior Publication Data
US 2023/0368903 A1 Nov. 16, 2023

(51) Int. Cl.
*G08C 17/04* (2006.01)
*G16H 20/13* (2018.01)
*G16H 40/40* (2018.01)
*H04B 5/70* (2024.01)

(52) U.S. Cl.
CPC ............. *G08C 17/04* (2013.01); *G16H 20/13* (2018.01); *G16H 40/40* (2018.01); *H04B 5/70* (2024.01); *G08C 2201/30* (2013.01)

(58) Field of Classification Search
CPC ................................ G08C 17/02; G08C 17/04
See application file for complete search history.

(56) References Cited

U.S. PATENT DOCUMENTS

2010/0217762 A1 8/2010 Kajio et al.
2012/0120259 A1 5/2012 Sakiyama et al.
2012/0209523 A1 8/2012 Nara et al.
(Continued)

FOREIGN PATENT DOCUMENTS

JP 2002-281573 A 9/2002
JP 2006-050521 A 2/2006
(Continued)

OTHER PUBLICATIONS

International Search Report for PCT Application No. PCT/JP2020/036777, mailed on Dec. 28, 2020.
(Continued)

*Primary Examiner* — Nabil H Syed
(74) *Attorney, Agent, or Firm* — Sughrue Mion, PLLC

(57) ABSTRACT

One of objects of the invention is to lower a possibility that operated equipment (101) is operated from an operation terminal (103) of a person who does not intend to operate the operated equipment (101). A communication control apparatus (102) includes a first wireless communication unit (110) that starts action of near-field wireless communication when acquiring a detection signal of a user or a target by a sensor (106) installed in the operated equipment (101) or an apparatus relating to the operated equipment (101), and an operation unit (111) that operates the operated equipment (101) by use of the first wireless communication unit (110), based on information from the operation terminal (103).

16 Claims, 10 Drawing Sheets

(56) References Cited

U.S. PATENT DOCUMENTS

| | | | | |
|---|---|---|---|---|
| 2015/0216201 A1* | 8/2015 | Bruckner | ............... | G07F 13/06 |
| | | | | 700/233 |
| 2016/0037332 A1* | 2/2016 | Egeler | .................. | H04W 4/029 |
| | | | | 455/420 |
| 2016/0112422 A1 | 4/2016 | Watanabe | | |
| 2016/0212194 A1 | 7/2016 | Palin et al. | | |
| 2017/0223218 A1 | 8/2017 | Su et al. | | |
| 2017/0372600 A1* | 12/2017 | Palin | ....................... | H04W 4/80 |
| 2019/0215411 A1 | 7/2019 | Komaki | | |
| 2022/0094778 A1* | 3/2022 | Khanna | ............... | G06K 7/1417 |

FOREIGN PATENT DOCUMENTS

| | | | |
|---|---|---|---|
| JP | 2008-042262 A | 2/2008 | |
| JP | 2008-042490 A | 2/2008 | |
| JP | 2009-116466 A | 5/2009 | |
| JP | 2010-130370 A | 6/2010 | |
| JP | 2010-273344 A | 12/2010 | |
| JP | 2012-105235 A | 5/2012 | |
| JP | 2017-214702 A | 12/2017 | |
| JP | 2018-182425 A | 11/2018 | |
| WO | 2022/070452 A1 | 4/2022 | |

OTHER PUBLICATIONS

JP Office Action for JP Application No. 2022-553436, mailed on Apr. 9, 2024 with English Translation.
JP Office Action for JP Application No. 2022-553243, mailed on Dec. 19, 2023 with English Translation.
JP Notice of Same Date Filing of Equivalent Applications by Same Applicant for JP Application No. 2022-553243, mailed on Dec. 19, 2023 with English Translation.
US Office Action for U.S. Appl. No. 18/027,002, mailed on Nov. 4, 2024.
US Office Action for U.S. Appl. No. 18/027,002, mailed on Apr. 17, 2025.

* cited by examiner

Figure 6:
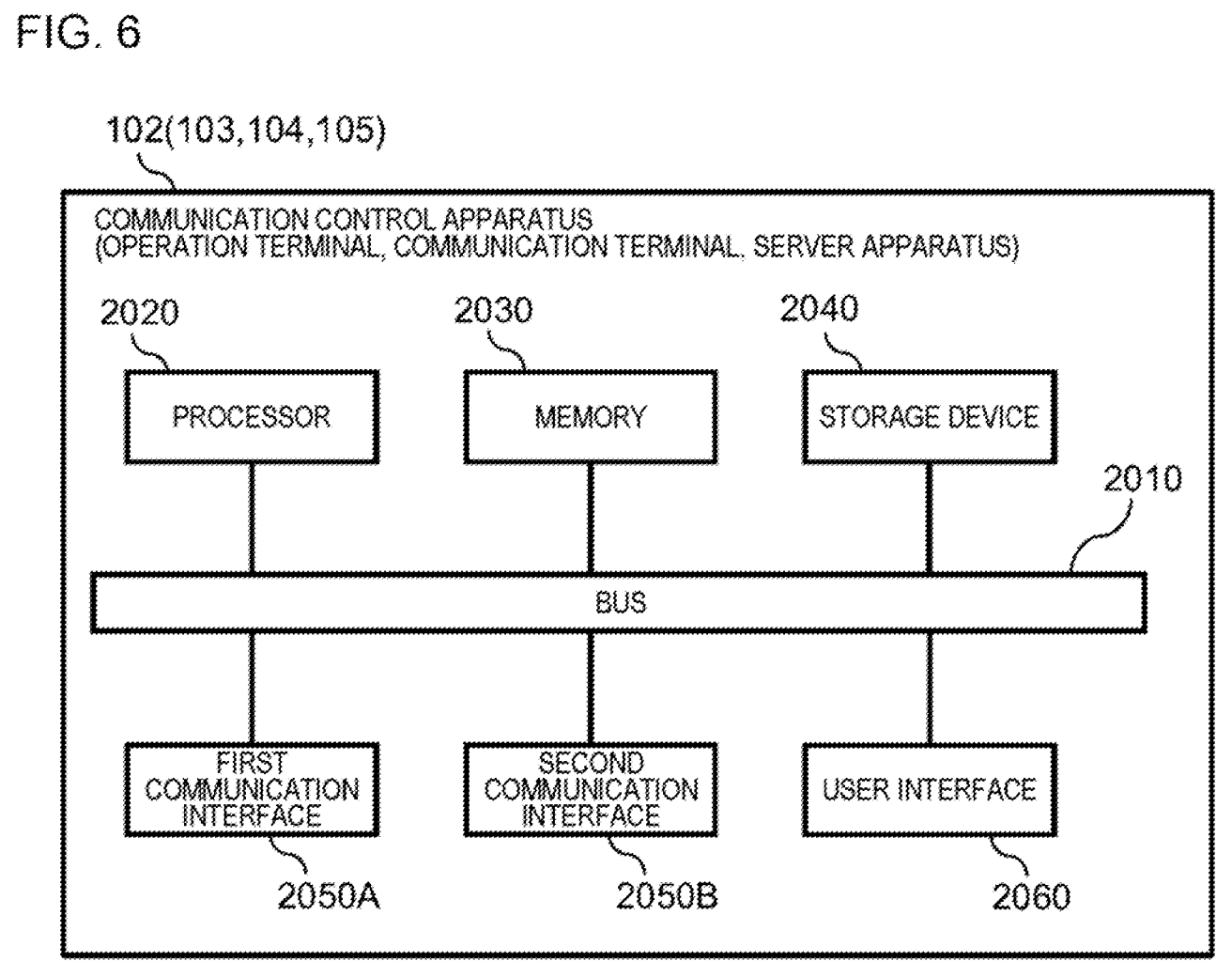

COMMUNICATION CONTROL APPARATUS
(OPERATION TERMINAL, COMMUNICATION TERMINAL, SERVER APPARATUS)

2020 PROCESSOR

2030 MEMORY

2040 STORAGE DEVICE

2010 BUS

2050A FIRST COMMUNICATION INTERFACE

2050B SECOND COMMUNICATION INTERFACE

2060 USER INTERFACE

FIG. 9

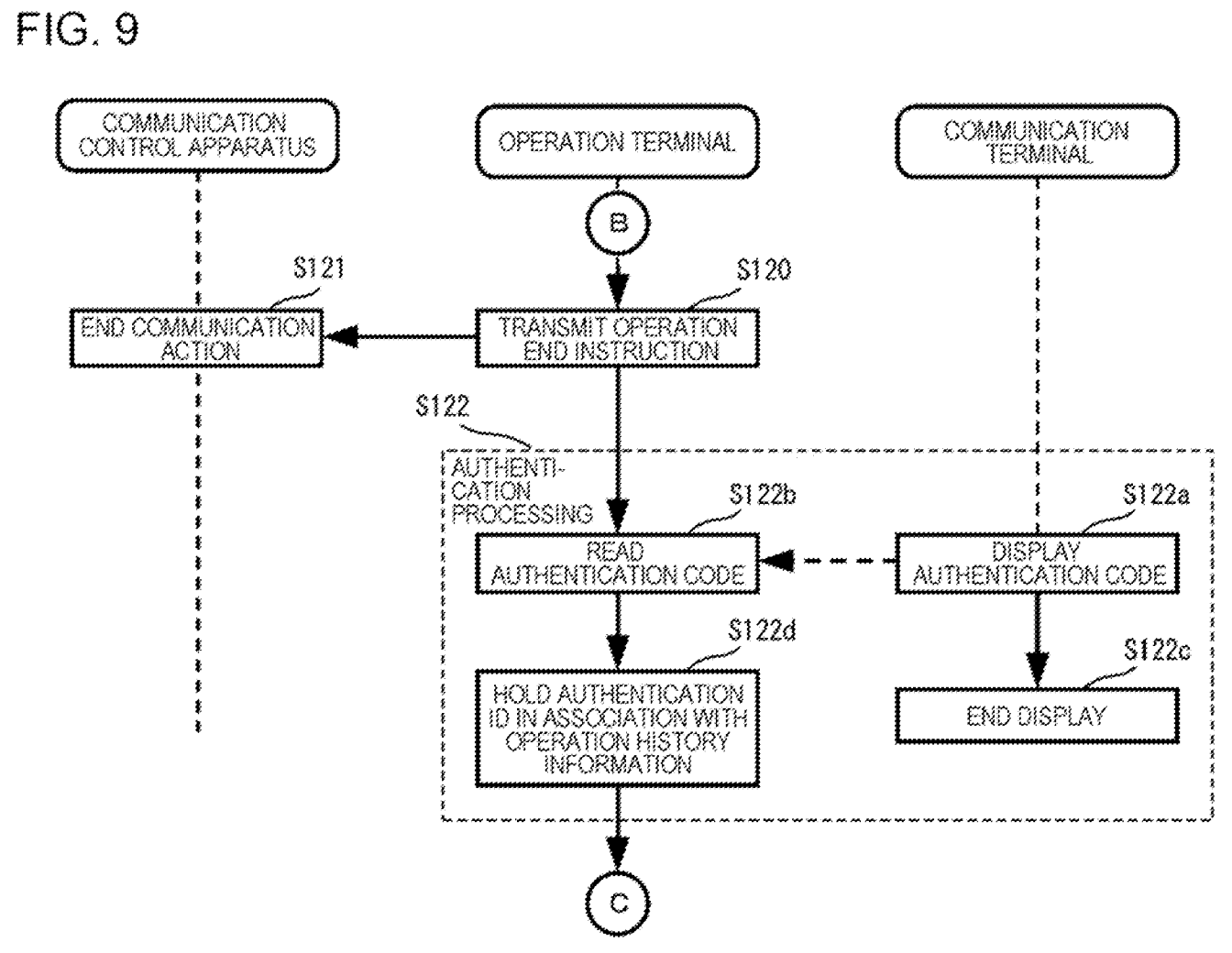

COMMUNICATION TERMINAL

DISPLAY AUTHENTICATION CODE    S122a

END DISPLAY    S122a

OPERATION TERMINAL

B

TRANSMIT OPERATION END INSTRUCTION    S120

AUTHENTICATION PROCESSING    S122

READ AUTHENTICATION CODE    S122b

HOLD AUTHENTICATION ID IN ASSOCIATION WITH OPERATION HISTORY INFORMATION    S122d

C

COMMUNICATION CONTROL APPARATUS

END COMMUNICATION ACTION    S121

FIG. 10

COMMUNICATION CONTROL APPARATUS, OPERATION TERMINAL, AND EQUIPMENT OPERATION SYSTEM

This application is a National Stage Entry of PCT/JP2020/036777 filed on Sep. 29, 2020, the contents of all of which are incorporated herein by reference, in their entirety.

TECHNICAL FIELD

The present invention relates to a communication control apparatus, an operation terminal, an equipment operation system, a communication control method, an operation terminal control method, and a program.

BACKGROUND ART

Various techniques for remotely operating operated equipment by an operation terminal including a communication function have been proposed.

For example, a remote operation system described in PTL 1 includes a mobile communication terminal having a touch panel type display and a wireless communication function, and operation target equipment remotely operated by a control signal wirelessly transmitted from the mobile communication terminal.

Further, the remote operation system described in PTL 1 includes a terminal recognition means for recognizing that the mobile communication terminal is present in a specific area where the operation target equipment is remotely operable. Then, on condition that recognition by the terminal recognition means is present, a dedicated operation screen for operating the operation target equipment is displayed on the touch panel type display of the mobile communication terminal.

PTL 1 describes that the remote operation system includes an entry sensing unit that senses entry of the mobile communication terminal into a room (area) where the operation target equipment is installed, and the mobile communication terminal and the entry sensing unit are each caused to function as the terminal recognition means.

RELATED DOCUMENT

Patent Document

[PTL 1] Japanese Patent Application Publication No. 2018-182425

SUMMARY OF THE INVENTION

Technical Problem

However, it is considered that, with the technique described in PTL 1, when an entry sensing unit constituting a terminal recognition means detects entry into the area, a dedicated operation screen is displayed on mobile communication terminals of all detected persons. Thus, there is a concern that a dedicated operation screen is displayed on a touch panel type display of even a mobile communication terminal of a person who does not intend to operate operation target equipment when the mobile communication terminal is in a specific area.

The present invention has been made in view of the situation described above, and one of objects thereof is to lower a possibility that operated equipment is operated from an operation terminal of a person who does not intend to operate the operated equipment.

Solution to Problem

In order to achieve the above object, a communication control apparatus according to a first aspect of the present invention includes:

a first wireless communication means for starting action of near-field wireless communication when acquiring a detection signal of a user or a target by a sensor installed in operated equipment or an apparatus relating to the operated equipment; and an operation means for operating the operated equipment by use of the first wireless communication means, based on information from the operation terminal.

In order to achieve the above object, an operation terminal according to a second aspect of the present invention includes:

an equipment information acquisition means for acquiring equipment information for identifying operated equipment;

an operation screen acquisition means for acquiring operation screen information relating to an operation screen of the operated equipment, by use of the equipment information;

an output means for outputting the operation screen information acquired by the operation screen acquisition means;

an operation history storage means for storing an operation history via the operation screen; and an operation history transmission means for transmitting, to an external apparatus, transmission information including at least one of identification information of an operation terminal and identification information of a user, and the operation history.

In order to achieve the above object, an equipment operation system according to a third aspect of the present invention includes:

a communication control apparatus and an operation terminal being capable of performing near-field wireless communication with each other, wherein the communication control apparatus includes a first wireless communication means for starting action of near-field wireless communication when acquiring a detection signal of a user or a target by a sensor installed in operated equipment or an apparatus relating to the operated equipment, and an operation means for operating the operated equipment by use of the first wireless communication means, based on information acquired from the operation terminal, and the operation terminal includes an equipment information acquisition means for acquiring equipment information for identifying the operated equipment, an operation screen display means for displaying an operation screen of the operated equipment, based on the equipment information, and an operation information transmission means for transmitting, to the first wireless communication means, the information according to an operation on the operation screen.

In order to achieve the above object, a communication control method according to a fourth aspect of the present invention includes, by a computer:

starting action of near-field wireless communication when acquiring a detection signal of a user or a target by a sensor installed in operated equipment or an apparatus relating to the operated equipment; and operating the operated equipment by use of the near-field wireless communication, based on information from the operation terminal.

In order to achieve the above object, a program according to a fifth aspect of the present invention causes a computer to execute:

starting action of near-field wireless communication when acquiring a detection signal of a user or a target by a sensor installed in operated equipment or an apparatus relating to the operated equipment; and operating the operated equipment by use of the near-field wireless communication, based on information from the operation terminal.

In order to achieve the above object, an operation terminal control method according to a sixth aspect of the present invention includes, by a computer:

acquiring equipment information for identifying operated equipment;

acquiring operation screen information relating to an operation screen of the operated equipment, by use of the equipment information;

outputting the operation screen information acquired by the operation screen acquisition means; and transmitting, to an external apparatus, transmission information including at least one of identification information of an operation terminal and identification information of a user, and an operation history via the operation screen.

In order to achieve the above object, a program according to a seventh aspect of the present invention causes a computer to execute:

acquiring equipment information for identifying operated equipment;

acquiring operation screen information relating to an operation screen of the operated equipment, by use of the equipment information;

outputting the operation screen information acquired by the operation screen acquisition means; and transmitting, to an external apparatus, transmission information including at least one of identification information of an operation terminal and identification information of a user, and an operation history via the operation screen.

Advantageous Effects of Invention

The present invention enables to lower a possibility that operated equipment is operated from an operation terminal of a person who does not intend to operate the operated equipment.

BRIEF DESCRIPTION OF THE DRAWINGS

FIG. 5 is a diagram illustrating one example of a physical configuration of the operated equipment.

FIG. 6 is a diagram illustrating one example of a physical configuration of the communication control apparatus.

FIG. 9 is a third diagram illustrating a flow of the equipment operation processing according to the one example embodiment of the present invention.

FIG. 10 is a fourth diagram illustrating a flow of the equipment operation processing according to the one example embodiment of the present invention.

DESCRIPTION OF EMBODIMENTS

Hereinafter, an example embodiment of the present invention is described by use of the drawings. Note that, in all of the drawings, a similar component is assigned with a similar reference sign, and description thereof is omitted, as appropriate.

<<Configuration of equipment operation system 100>>

An equipment operation system 100 according to one example embodiment of the present invention is a system for operating operated equipment 101 from an operation terminal 103 of a user.

Figure 1:
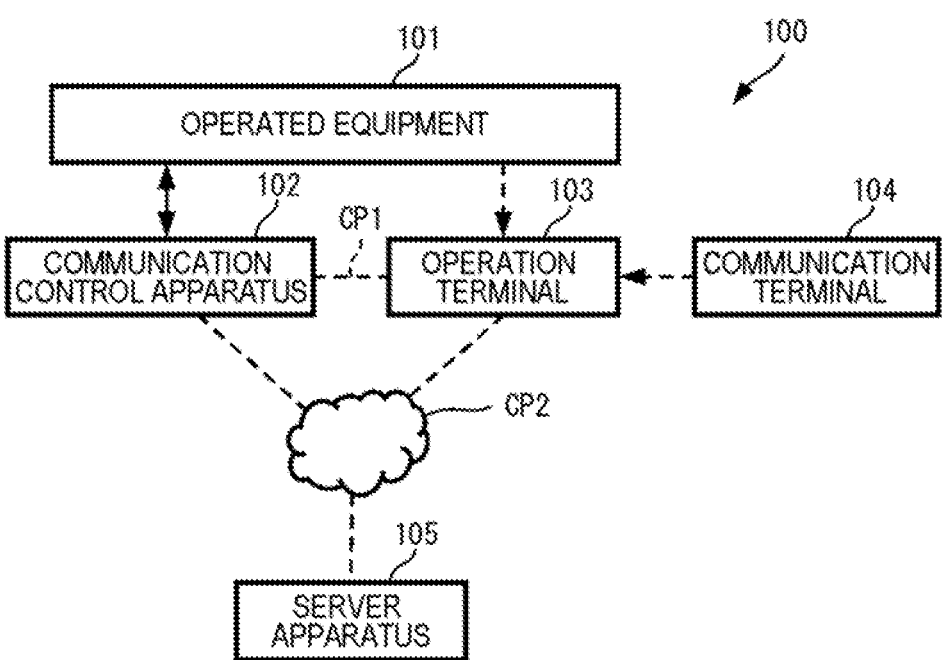
FIG. 1 is a diagram illustrating a configuration of an equipment operation system according to one example embodiment of the present invention.

As illustrated in FIG. 1, the equipment operation system 100 includes the operated equipment 101 to be operated by a user, a communication control apparatus 102 that is connected to the operated equipment 101 and controls communication of the operated equipment 101, the operation terminal 103 for operating the operated equipment 101, a communication terminal 104 for authenticating an operation of the operated equipment 101 from the operation terminal 103, and a server apparatus 105 for holding an operation history.

As the operated equipment 101, for example, equipment having a possibility of being operated by different users, such as medical equipment or a vending machine for a beverage, is preferably adopted. The communication control apparatus 102 and the operation terminal 103 are configured to be communicable with each other via a first communication path CP1.

The first communication path CP1 is a communication path for performing near-field wireless communication such as Bluetooth (registered trademark) and infrared communication.

By operating the operated equipment 101 from the operation terminal 103 of a user via the first communication path CP1 and the communication control apparatus 102, a chance where different users touch the operated equipment 101 can be reduced. This enables to lower contamination of the operated equipment 101 with a bacterium, a virus, or the like due to contact of a hand or the like of the user.

Moreover, the communication control apparatus 102, the operation terminal 103, and the server apparatus 105 are configured to be communicable with one another via a second communication path CP2.

The second communication path CP2 is a communication path, such as a local area network (LAN) and a wide area network (WAN), being communicable in a wider area than the first communication path CP1, and is constructed including a wireless communication line. Note that, the second communication path CP2 may be constructed including a wired communication line, as appropriate.

Further, the operation terminal 103 can acquire information from each of the communication terminal 104 and the operated equipment 101 by reading a code displayed on each of the communication terminal 104 and the operated equipment 101.

The code is, for example, a one-dimensional or two-dimensional bar code.

<Functional Configuration of Operated Equipment 101>

Figure 2:
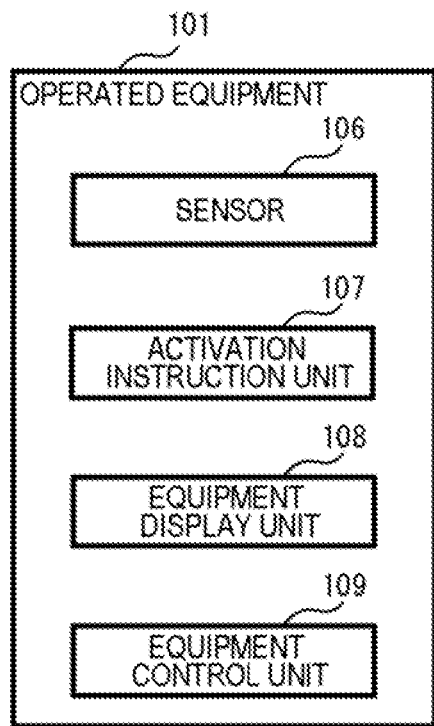
FIG. 2 is a diagram illustrating a functional configuration of operated equipment according to the one example embodiment.

Functionally, as illustrated in FIG. 2, the operated equipment 101 includes a sensor 106, an activation instruction unit 107, an equipment display unit 108, and an equipment control unit 109.

The sensor 106 is a sensor for detecting proximity of a user to a predetermined range (e.g., within one meter), and outputs a detection signal when a user or a predetermined target is detected.

The sensor 106 may be a human sensor or the like provided in the operated equipment 101, or may be a sensor provided in relation to the operated equipment 101, such as a camera that captures a region where the operated equipment 101 is installed. Moreover, when the operated equipment 101 is a vending machine of a beverage, the sensor 106 may be a sensor that recognizes, as a target, a container into which the beverage is injected, and detects that the container is placed in a predetermined position.

When the activation instruction unit 107 acquires the detection signal from the sensor 106, the activation instruction unit 107 outputs an activation instruction to the communication control apparatus 102. The activation instruction is an instruction for causing the communication control apparatus 102 to start action of near-field wireless communication via the first communication path CP1.

The equipment display unit 108 is a screen that displays information, and displays, for example, an equipment code. The equipment code is a code including equipment information (hereinafter, also referred to as an "equipment ID") for identifying the operated equipment 101.

The equipment control unit 109 controls action of the operated equipment 101.

Figure 3:
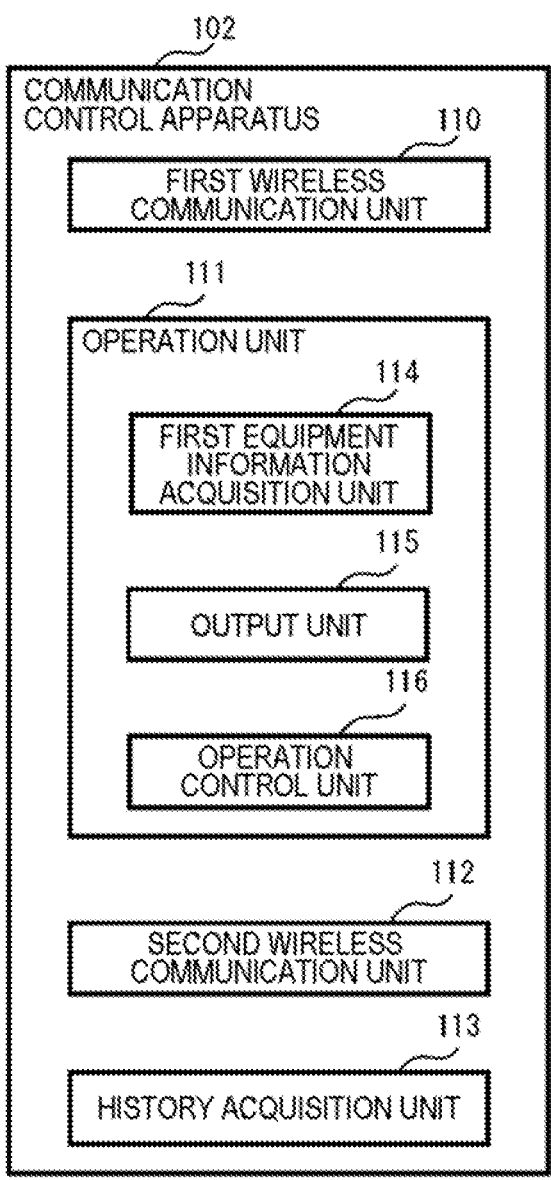
FIG. 3 is a diagram illustrating a functional configuration of a communication control apparatus according to the one example embodiment.

Functionally, as illustrated in FIG. 3, the communication control apparatus 102 includes a first wireless communication unit 110, an operation unit 111, a second wireless communication unit 112, and a history acquisition unit 113.

The first wireless communication unit 110 mutually communicates with the operation terminal 103 via the first communication path CP1, as a first wireless communication means of the communication control apparatus 102.

Specifically, the first wireless communication unit 110 starts action of near-field wireless communication when an activation instruction is acquired. In other words, when the first wireless communication unit 110 acquires a detection signal of a user or a target by the sensor 106, the first wireless communication unit 110 starts action of near-field wireless communication.

Moreover, when the first wireless communication unit 110 accepts an operation end instruction, the first wireless communication unit 110 ends an operation of the near-field wireless communication. The operation end instruction is an instruction indicating that an operation of the operated equipment 101 is terminated, and is output from the operation terminal 103.

The operation unit 111 operates the operated equipment 101, based on information from the operation terminal 103 acquired via the first communication path CP1, by using the first wireless communication unit 110.

Specifically, the operation unit 111 includes a first equipment information acquisition unit 114, an output unit 115, and an operation control unit 116.

The first equipment information acquisition unit 114 acquires, as an acquisition means, an equipment ID from the operation terminal 103 via the first communication path CP1. For example, the first equipment information acquisition unit 114 acquires the equipment ID from the operation terminal 103 that has acquired the equipment ID included in an equipment code by reading the equipment code.

The output unit 115 outputs operation screen information to the operation terminal 103 via the first communication path CP1, based on the equipment ID acquired by the first equipment information acquisition unit 114. The operation screen information is information relating to an operation screen of the operated equipment 101 according to an equipment ID.

When the operation control unit 116 acquires operation information from the operation terminal 103 via the first communication path CP1, the operation control unit 116 outputs the operation information to the operated equipment 101. The operation information is information for operating the operated equipment 101, and the equipment control unit 109 that has acquired the operation information controls action of the operated equipment 101, based on the operation information.

The second wireless communication unit 112 mutually communicates with the operation terminal 103 via the second communication path CP2. In other words, the second wireless communication unit 112 performs wireless communication by a route being different from that of the first wireless communication unit 110, as a second wireless communication means of the communication control apparatus 102.

The history acquisition unit 113 acquires operation history information from the operation terminal 103 via the second communication path CP2, i.e., the second wireless communication unit 112 being different from the first wireless communication unit 110.

The operation history information includes an operation ID, and an operation history of the operated equipment 101. The operation ID is information for identifying a user who has operated the operated equipment 101, and includes, for example, at least one of identification information of the operation terminal 103 (hereinafter, also referred to as an "operation terminal ID") and identification information of a user (hereinafter, referred to as a "user ID").

The history acquisition unit 113 according to the present example embodiment acquires, from the operation terminal 103, transmission information including communication history information in addition to operation history information.

The communication history information is information relating to a communication history between the operation terminal 103 and the communication terminal 104 being different from the operation terminal 103. The communication history includes identification information of the communication terminal 104 (details are described later.), and a communication time between the communication terminal 104 and the operation terminal 103.

In other words, the history acquisition unit 113 according to the present example embodiment acquires operation history information including an operation ID and an operation history, from the operation terminal 103 via the second wireless communication unit 112, as a communication history acquisition means. Moreover, the history acquisition unit 113 according to the present example embodiment acquires communication history information as a communication history acquisition unit of the communication control apparatus 102.

<Functional Configuration of Operation Terminal 103>

Figure 4:
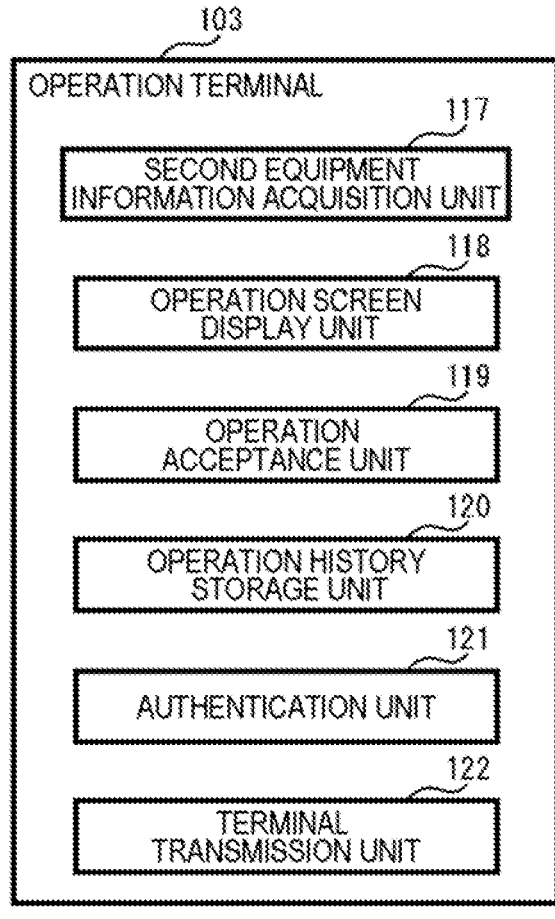
FIG. 4 is a diagram illustrating a functional configuration of an operation terminal according to the one example embodiment.

Functionally, as illustrated in FIG. 4, the operation terminal 103 includes a second equipment information acquisition unit 117, an operation screen display unit 118, an operation acceptance unit 119, an operation history storage unit 120, an authentication unit 121, and a terminal transmission unit 122.

The second equipment information acquisition unit 117 acquires an equipment ID, as an equipment information acquisition means of the operation terminal 103.

The second equipment information acquisition unit 117 according to the present example embodiment includes a camera, and acquires an equipment ID included in an equipment code, by reading the equipment code displayed on the equipment display unit 108. The second equipment information acquisition unit 117 transmits the equipment ID to the communication control apparatus 102 via the first communication path CP1.

Note that, the second equipment information acquisition unit 117 is not limited to a camera, and may be configured in such a way as to acquire an equipment ID from the operated equipment 101 by infrared communication or the like.

The operation screen display unit 118 is a touch panel, a screen, or the like according to an equipment ID that displays an operation screen of the operated equipment 101.

The operation screen display unit 118 according to the present example embodiment acquires operation screen information output from the output unit 115 by use of the equipment ID, as an operation screen acquisition means. Moreover, the operation screen display unit 118 displays the acquired operation screen information, as an output means of the operation terminal 103.

The operation acceptance unit 119 performs processing for operating the operated equipment 101, based on an operation of a user on the operation screen.

Specifically, the operation acceptance unit 119 accepts an operation of a user on the operation screen until an instruction to end an operation of the operated equipment 101 (operation end instruction) is accepted from the user, and generates operation information according to the operation. The operation acceptance unit 119 transmits the generated operation information to the communication control apparatus 102, as an operation information transmission means.

Moreover, the operation acceptance unit 119 holds an operation history of the operated equipment 101, and, when an operation end instruction is accepted, the operation acceptance unit 119 generates operation history information associating an operation terminal ID of the operation terminal 103 with an operation history, and causes the operation history storage unit 120 to hold the generated operation history information.

The operation history storage unit 120 is a storage unit for storing the operation history via the operation screen. The operation history storage unit 120 according to the present example embodiment holds operation history information.

The authentication unit 121 performs processing for acquiring, by a user of the operation terminal 103, authentication, regarding an operation of the operated equipment 101, by an authenticator being a user of the communication terminal 104 and having witnessed the operation.

Specifically, the authentication unit 121 includes a camera, and acquires, by reading an authentication code displayed on the communication terminal 104, identification information of the communication terminal 104 included in the authentication code (hereinafter, also referred to as an "authentication ID"). The authentication unit 121 generates communication history information by associating, with the acquired authentication ID, a communication time with the communication terminal 104.

The authentication ID is information for identifying an authenticator, and, in the present example embodiment, identification information of the communication terminal 104 utilized by the authenticator is adopted as the authentication ID. Note that, the authentication ID may be identification information of the authenticator (authenticator ID).

Note that, the authentication unit 121 is not limited to a camera, and may be configured in such a way as to acquire an authentication ID from the operated equipment 101 by infrared communication or the like.

The terminal transmission unit 122 generates transmission information including operation history information held in the operation history storage unit 120 and communication history information generated by the authentication unit 121, as an operation history transmission means. Then, the terminal transmission unit 122 transmits the generated transmission information to the communication control apparatus 102 and the server apparatus 105, by use of the second wireless communication unit 112 being different from the first wireless communication unit 110, i.e., via the second communication path CP2.

<Functional Configuration of Communication Terminal 104>

FIG. 1 is referred to again.

The communication terminal 104 displays a code including an authentication ID, according to an operation of an authenticator.

<Functional Configuration of Server Apparatus 105>

The server apparatus 105 is an apparatus that manages the equipment operation system 100, acquires transmission information from the operation terminal 103 via the second communication path CP2, and stores the acquired transmission information.

<Physical Configuration of Operated Equipment 101>

As described above, physically, as illustrated in FIG. 5, the operated equipment 101 is medical equipment, a vending machine, or the like, and includes the sensor 106, a bus 1010, a processor 1020, a memory 1030, a storage device 1040, a communication interface 1050, a display unit 1060, and an input unit 1070.

Figure 5:
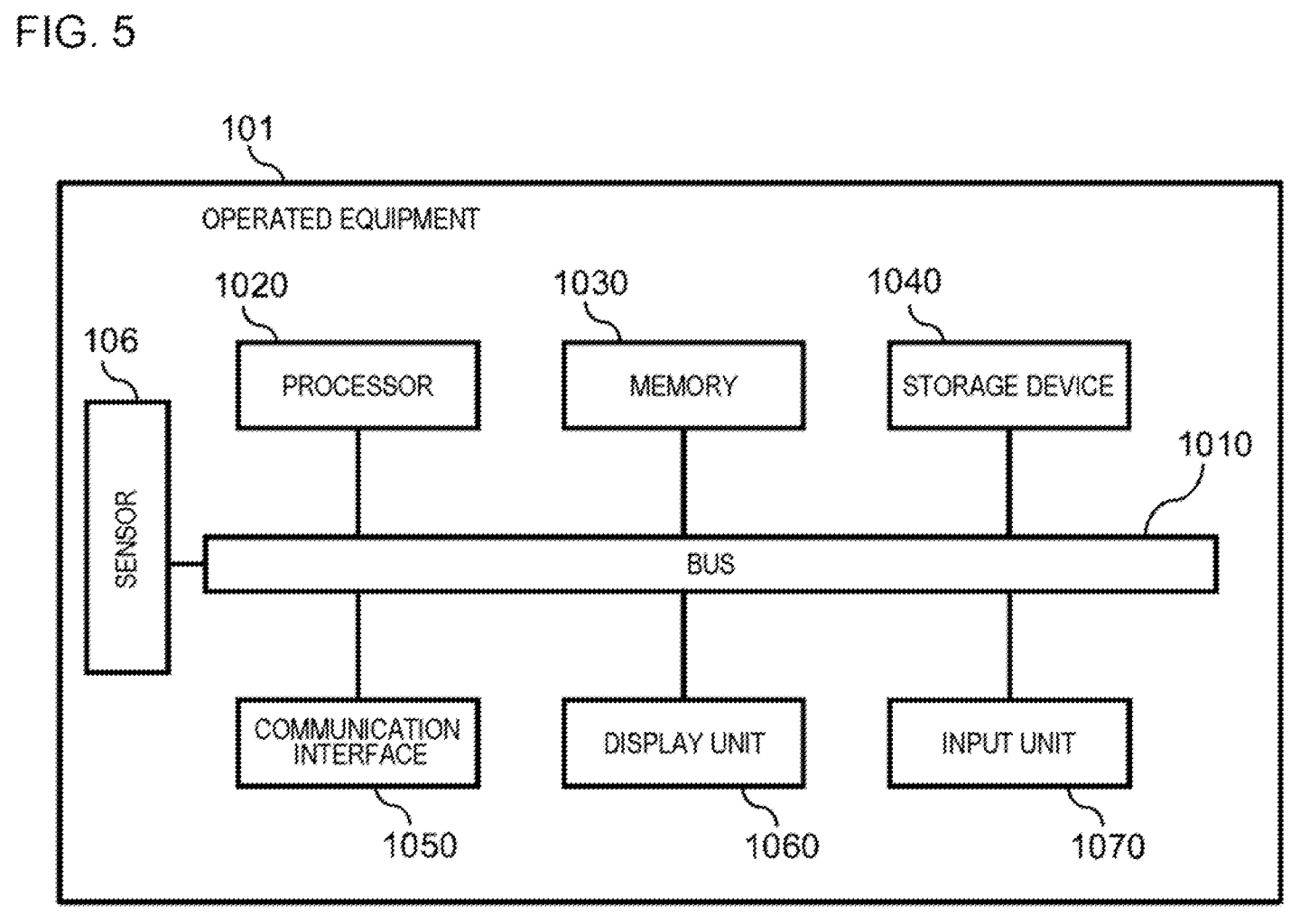

Note that, as described above, the operated equipment 101 is medical equipment, a vending machine, or the like, and a mechanism or an apparatus (e.g., an X-ray radiation unit in a case of an X-ray apparatus, a pump in a case of a vending machine that injects a beverage into a container, or the like) according to the function of the equipment is omitted in FIG. 5.

The bus 1010 is a data transmission path through which the sensor 106, the processor 1020, the memory 1030, the storage device 1040, the communication interface 1050, the display unit 1060, and the input unit 1070 transmit/receive data to/from one another. However, a method of mutually connecting the processor 1020 and the like is not limited to bus connection.

The processor 1020 is a processor achieved by a central processing unit (CPU), a graphics processing unit (GPU), or the like.

The memory 1030 is a main storage apparatus achieved by a random access memory (RAM) or the like.

The storage device 1040 is an auxiliary storage apparatus achieved by a hard disk drive (HDD), a solid state drive (SSD), a memory card, a read only memory (ROM), or the like. The storage device 1040 stores a program module for achieving each function of the operated equipment 101. The processor 1020 reads each of the program modules onto the memory 1030, executes the read program module, and thereby achieves each functional unit being relevant to the program module.

The communication interface 1050 is an interface for communicating of the operated equipment 101.

The display unit 1060 is a portion that displays information to a user, and is configured by, for example, a liquid crystal panel or the like.

The input unit 1070 is a portion for inputting by a user, and is configured by, for example, a touch sensor provided on a screen of the liquid crystal panel, a keyboard, a mouse, or the like.

<Physical Configuration of Communication Control Apparatus 102>

Physically, as illustrated in FIG. 6, the communication control apparatus 102 includes a bus 2010, a processor 2020, a memory 2030, a storage device 2040, a first communication interface 2050A, a second communication interface 2050B, and a user interface 2060.

The bus 2010 is a data transmission path through which the processor 2020, the memory 2030, the storage device 2040, the first communication interface 2050A, the second communication interface 2050B, and the user interface 2060 transmit/receive data to/from one another. However, a method of mutually connecting the processor 2020 and the like is not limited to bus connection.

The processor 2020 is a processor achieved by a central processing unit (CPU), a graphics processing unit (GPU), or the like.

The memory 2030 is a main storage apparatus achieved by a random access memory (RAM) or the like.

The storage device 2040 is an auxiliary storage apparatus achieved by a hard disk drive (HDD), a solid state drive (SSD), a memory card, a read only memory (ROM), or the like. The storage device 2040 stores a program module for achieving each function of the communication control apparatus 102. The processor 2020 reads each of the program modules onto the memory 2030, executes the read program module, and thereby achieves each functional unit being relevant to the program module.

The first communication interface 2050A is an interface for performing communication via the first communication path CP1.

The second communication interface 2050B is an interface for performing communication via the second communication path CP2 being different from the first communication path CP1.

The user interface 2060 is a portion for displaying information to a user, and for inputting by a user, and is configured by, for example, a liquid crystal panel, a touch sensor provided on a screen of the liquid crystal panel, a keyboard, a mouse, or the like. Further, the user interface 2060 may include a speaker that emits sound.

Note that, the communication control apparatus 102 itself may not include the user interface 2060, and, in this case, for example, a personal computer, a tablet terminal, or the like may be connected via the first communication interface 2050A, the second communication interface 2050B, a universal serial bus (USB) port, or the like, as the user interface 2060 of the communication control apparatus 102, according to need.

Moreover, a functional and physical configuration of the communication control apparatus 102 may be physically and functionally incorporated in the operated equipment 101, and, in this case, the operated equipment 101 becomes a communication control apparatus.

<Physical Configurations of Operation Terminal 103, Communication Terminal 104, and Server Apparatus 105>

Each of the operation terminal 103 and the communication terminal 104 is configured by, for example, a tablet terminal, a smartphone, or the like in which an application program is previously installed. Moreover, for example, the server apparatus 105 is configured by a personal computer or the like in which an application program is previously installed.

Each of the physical components of each of the operation terminal 103, the communication terminal 104, and the server apparatus 105 may be substantially similar to that of the communication control apparatus illustrated in FIG. 6. In order to make description brief, detailed description relating to a physical configuration of each of the operation terminal 103, the communication terminal 104, and the server apparatus 105 is omitted.

Note that, the communication terminal 104 may not include the communication interfaces 2050A and 2050B. Moreover, the server apparatus 105 may not include the first communication interface 2050A.

So far, the configuration of the equipment operation system 100 has been described. From now on, action of the equipment operation system 100 is described with reference to the drawings.

<<Action of Equipment Operation System 100>>

FIGS. 7 to 10 are diagrams illustrating a flow of equipment operation processing executed by the equipment operation system 100 according to the present example embodiment. The equipment operation processing is started, for example, in a state where a predetermined program module of each of the operated equipment 101, the communication control apparatus 102, the communication terminal 104, and the server apparatus 105 is executed, and the operation terminal 103 is run. At a time of start of the equipment operation processing, the first wireless communication unit 110 of the communication control apparatus 102 stops action for performing near-field wireless communication via the first communication path CP1, and waits for acceptance of an activation instruction.

Figure 7:
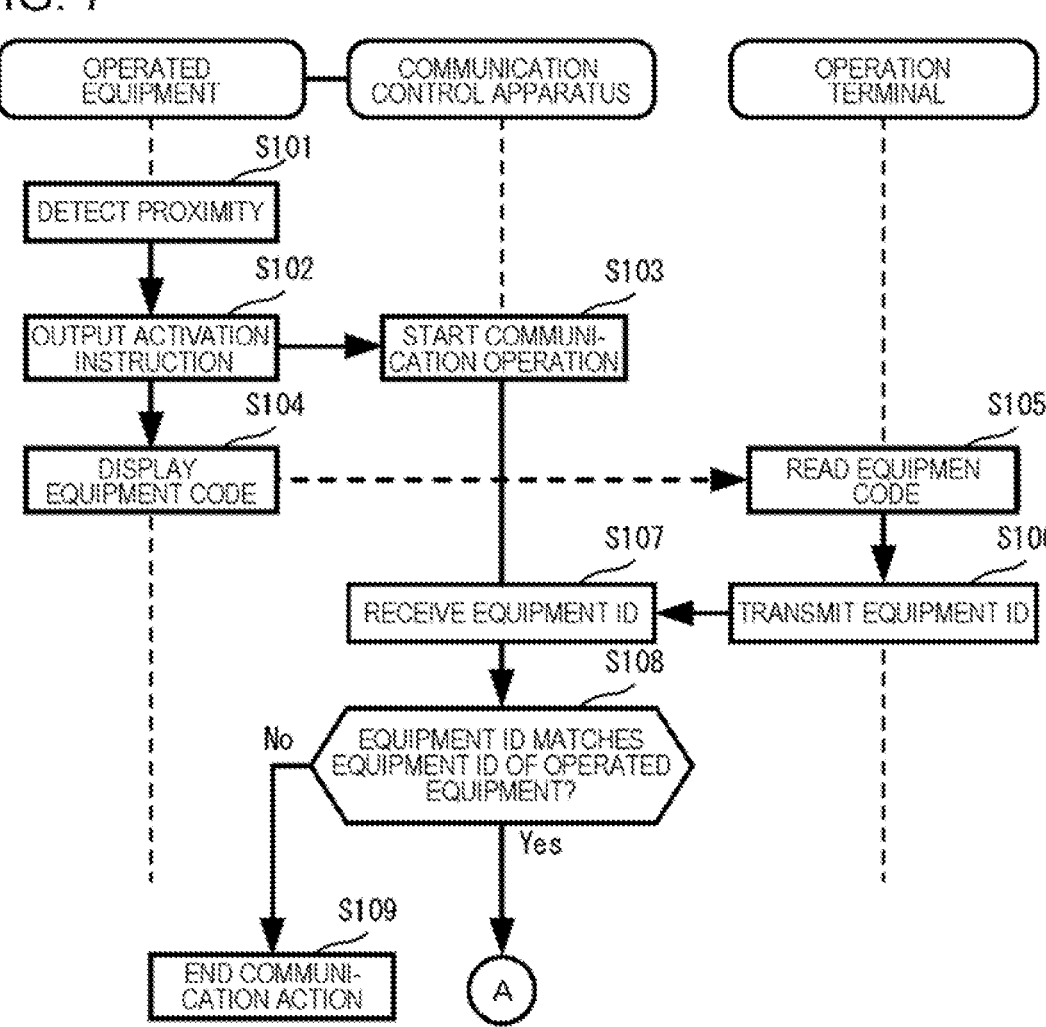
FIG. 7 is a first diagram illustrating a flow of equipment operation processing according to the one example embodiment of the present invention.

As illustrated in FIG. 7, the sensor 106 detects a user or a predetermined target (step S101). Thereby, the sensor 106 outputs a detection signal.

When the activation instruction unit 107 acquires the detection signal output in step S101, the activation instruction unit 107 outputs an activation instruction to the communication control apparatus 102 (step S102).

When the first wireless communication unit 110 acquires the activation instruction output in step S102, the first wireless communication unit 110 starts the action of near-field wireless communication (step S103).

On the other hand, the equipment display unit 108 displays an equipment code including an equipment ID of the operated equipment 101 on a screen after step S103 (step S104). In other words, the equipment code including the equipment ID is output to the screen of the operated equipment 101 when the action of the near-field wireless communication is started.

In this way, by displaying an equipment code including an equipment ID on a screen, it becomes possible to save a trouble of individually attaching, to the operated equipment 101, for example, a sticker or the like having the equipment code printed thereon. Moreover, by displaying an equipment code on the screen, it becomes easy to recognize the equipment code in the operation terminal 103, and, therefore, it becomes possible to lessen a possibility of erroneously reading the equipment code. Further, when there is a change of an equipment ID, an equipment code can be easily changed, and, therefore, it becomes possible to easily respond to a change of the equipment ID.

A camera captures the equipment code displayed on the equipment display unit 108 in step S104, and, thereby, the second equipment information acquisition unit 117 reads the equipment code (step S105).

In this instance, the operation terminal 103 detects that the equipment code has been read by the camera in step S105, and activates a predetermined program module. Note that, the program module of the operation terminal 103 may be executed from the time of start of the equipment operation processing.

Moreover, the operation terminal 103 may include a payment unit that automatically makes a payment via the second communication path CP2, and, in this case, when it is detected that the equipment code has been read by the camera in step S105, the payment unit may perform payment processing of a purchased product or service according to need.

The second equipment information acquisition unit 117 acquires an equipment ID, based on the equipment code read in step S105. Then, the second equipment information acquisition unit 117 transmits the acquired equipment ID to the communication control apparatus 102 via the first communication path P1 (step S106).

The first equipment information acquisition unit 114 acquires the equipment ID transmitted in step S106 via the first communication path CP1 (step S107).

The output unit 115 determines whether the equipment ID acquired in step S107 matches a previously registered equipment ID of the operated equipment 101 (step S108). When the equipment IDs do not match (step S108; No), the output unit 115 ends the equipment operation processing (step S109).

Figure 8:
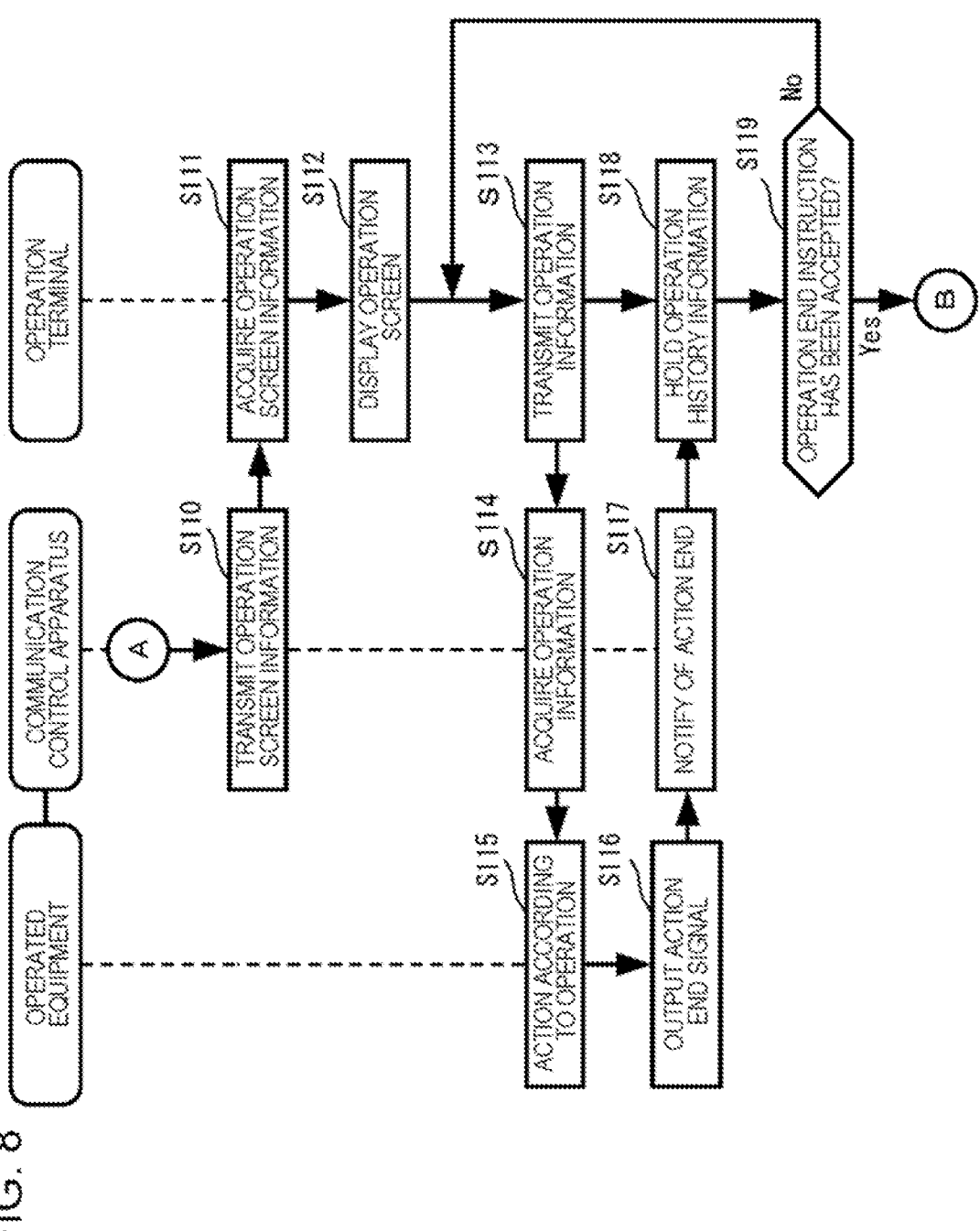
FIG. 8 is a second diagram illustrating a flow of the equipment operation processing according to the one example embodiment of the present invention.

When the equipment IDs match (step S108; Yes), the output unit 115 transmits operation screen information relating to an operation screen of the operated equipment 101 according to the equipment ID, to the operation terminal 103 via the first communication path P1 (step S110), as illustrated in FIG. 8.

The operation screen display unit 118 acquires, via the first communication path P1, the operation screen information transmitted in step S110 (step S111). Then, the operation screen display unit 118 displays the operation screen indicated by the operation screen information acquired in step S111 (step S112).

When the operation acceptance unit 119 accepts an operation of a user on the operation screen, the operation acceptance unit 119 transmits operation information according to the operation, to the communication control apparatus 102 via the first communication path P1 (step S113).

When the operation control unit 116 acquires the operation information transmitted in step S113, from the operation terminal 103 via the first communication path CP1 (step S114), the operation control unit 116 outputs the operation information to the operated equipment 101. In this instance, a format or the like of the operation information may be converted by the operation control unit 116, as appropriate.

When the equipment control unit 109 acquires the operation information output in step S114, the equipment control unit 109 causes the operated equipment 101 to act, by controlling according to the operation information (step S115).

When the action based on the operation information in step S115 ends, the equipment control unit 109 outputs, to the communication control apparatus 102, an action end signal for notifying of the end (step S116).

When the equipment control unit 109 acquires the action end signal output in step S116, the equipment control unit 109 notifies the operation terminal 103 of the end of the action based on the operation information transmitted in immediately preceding step S113, via the first communication path P1 (step S117).

When the operation acceptance unit 119 acquires the notification output in step S117, the operation acceptance unit 119 holds, as operation history information, an operation history including an operation indicated by the operation information transmitted in immediately preceding step S113, and a time of the operation (step S118).

The operation acceptance unit 119 determines whether an operation end instruction has been accepted, based on an operation of a user (step S119). When the operation acceptance unit 119 determines that the operation end instruction is not accepted (step S119; No), processing in steps S113 to S118 are repeatedly executed.

When the operation acceptance unit 119 determines that the operation end instruction has been accepted (step S119; Yes), the operation acceptance unit 119 generates operation history information associating an operation terminal ID of the operation terminal 103 with the operation history held in step S118, and causes the operation history storage unit 120 to hold the generated operation history information.

Subsequently, as illustrated in FIG. 9, the operation acceptance unit 119 transmits the operation end instruction to the operation control unit 116 via the first communication path CP1 (step S120).

When the first wireless communication unit 110 acquires the operation end instruction transmitted in step S120, the first wireless communication unit 110 ends a communication action for communicating with the operation terminal 103 via the first communication path CP1 (step S121).

Thereby, the near-field wireless communication between the communication control apparatus 102 and the operation terminal 103 via the first communication path CP1 ends. Then, the operated equipment 101 and the communication control apparatus 102 return to a state similar to that at the time of start of the equipment operation processing, and the first wireless communication unit 110 waits for acceptance of the activation instruction.

The operation terminal 103 and the communication terminal 104 perform authentication processing (step S122). The authentication processing is processing for authenticating, by an authenticator, an operation on the operated equipment 101 by a user of the operation terminal 103.

In the authentication processing (step S122), specifically, the communication terminal 104 displays an authentication code including an authentication ID, according to an operation of the authenticator (step S122*a*).

A camera captures the authentication code displayed in step S122*a*, and, thereby, the authentication unit 121 reads the authentication code (step S122*b*).

The communication terminal 104 ends display of the authentication code, for example, when a predetermined time elapses (step S122c).

The authentication unit 121 acquires the authentication ID included in the authentication code read in step S122b, and associates the acquired authentication ID with the operation history information held in the operation history storage unit 120 after determination processing in step S119. Thereby, the authentication unit 121 causes the operation history storage unit 120 to hold the authentication ID in association with the operation history information (step S122d).

Thereby, the authentication processing ends (step S122).

Figure 10:
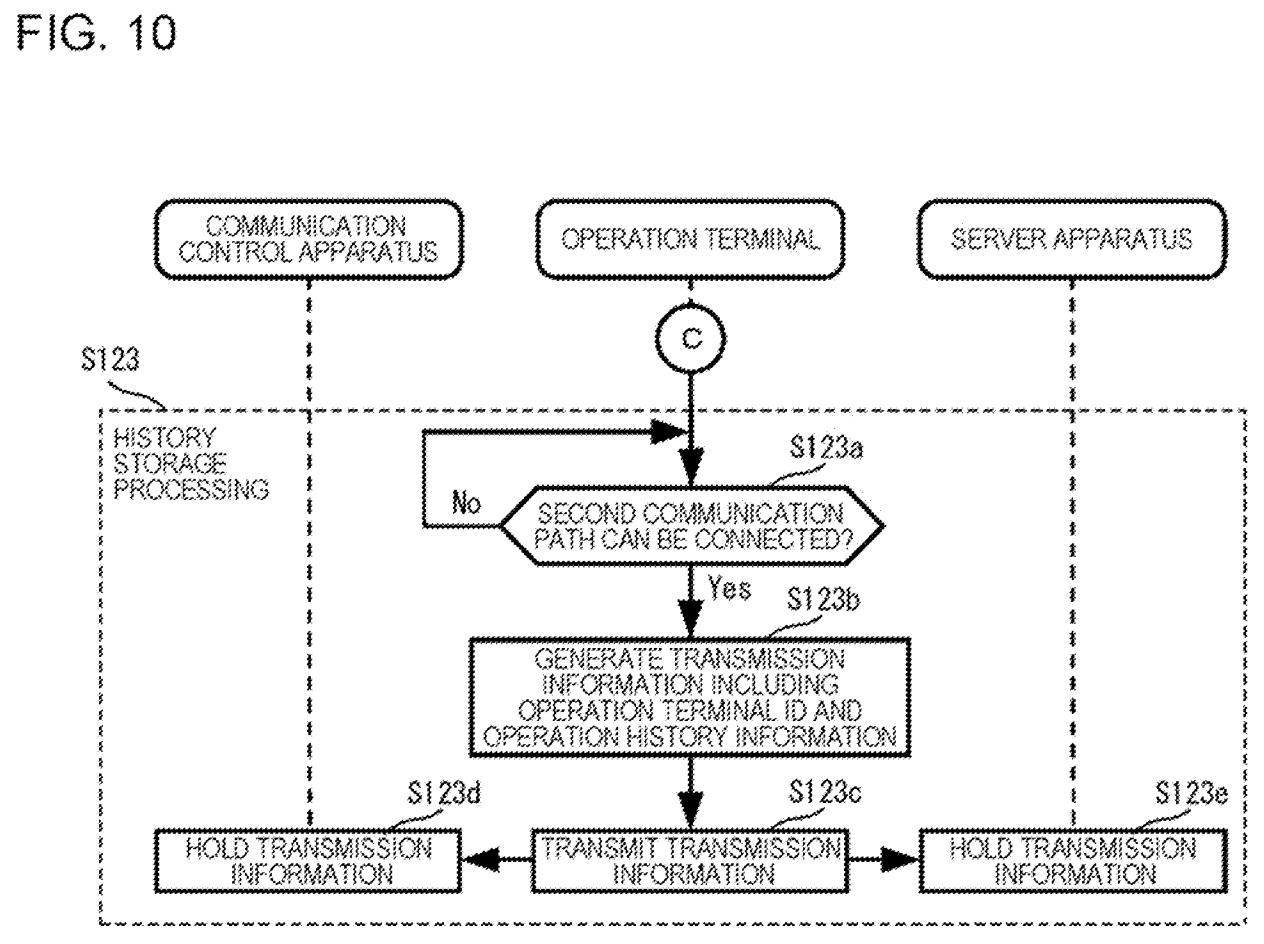

Subsequently, as illustrated in FIG. 10, the operation terminal 103, the communication control apparatus 102, and the server apparatus 105 execute history storage processing (step S123). The history storage processing (step S123) is processing for causing an apparatus other than the operation terminal 103 to hold operation history information including an operation history and the like.

The terminal transmission unit 122 determines whether the second communication path CP2 can be connected (step S123a). The terminal transmission unit 122 determines whether the second communication path CP2 can be connected, based on, for example, whether the operation terminal 103 is in an environment of being capable of transmitting and receiving radio for connecting to the second communication path CP2.

For example, when the operation terminal 103 is not in an environment of being capable of transmitting and receiving radio for connecting to the second communication path CP2, the terminal transmission unit 122 determines that the second communication path CP2 may not connected (step S123a; No). In this case, the terminal transmission unit 122 executes determination processing in step S123a continuously or intermittently at a predetermined time interval until an environment becomes such that the second communication path CP2 can be connected.

For example, when the operation terminal 103 is in an environment of being capable of transmitting and receiving radio for connecting to the second communication path CP2, the terminal transmission unit 122 determines that the second communication path CP2 can be connected (step S123a; Yes). In this case, the terminal transmission unit 122 generates transmission information including the operation terminal ID of the operation terminal 103 and the operation history information (i.e., operation history information with which the authentication ID is associated) held in step S122d (step S123b).

The terminal transmission unit 122 transmits the transmission information generated in step S123b to each of the communication control apparatus 102 and the server apparatus 105 via the second communication path CP2 (step S123c).

Thereby, a communication path being different from the first communication path CP1 can be selected as a communication path for transmitting transmission information. Thus, a communication path being suitable for a data size can be selected, and, even when a data size of transmission information becomes relatively large, it becomes possible to stably transmit the transmission information in a relatively short time.

When the history acquisition unit 113 acquires the transmission information transmitted in step S123c, the history acquisition unit 113 holds operation history information including the transmission information and a communication time for acquiring the transmission information (step S123d).

When the server apparatus 105 acquires the transmission information transmitted in step S123c, the server apparatus 105 also holds the operation history information including the transmission information and the communication time for acquiring the transmission information (step S123e). The operation terminal 103 erases, from a storage unit of the operation terminal 103, the equipment code read in step S105 and the equipment ID included in the equipment code. Thereby, the communication control apparatus 102, the operation terminal 103, and the server apparatus 105 end the equipment operation processing.

According to the present example embodiment, when a detection signal of a user or a target is acquired by the sensor 106, action of near-field wireless communication is started. Thus, the operation terminal 103 that can operate the operated equipment 101 can be limited to the operation terminal 103 of a person detected by the sensor 106 or a person being related to a target. Therefore, it becomes possible to lower a possibility that the operated equipment 101 is operated from an operation terminal of a person who does not intend to operate the operated equipment 101.

Although the one example embodiment and the modified example of the present invention have been described above with reference to the drawings, the example embodiment and the modified example are exemplifications of the present invention, and may be changed as appropriate.

For example, when processing of the operated equipment 101 being relevant to an operation from the operation terminal 103, such as injection of a beverage into a container in a case where the operated equipment 101 is a vending machine for the beverage, ends, the first wireless communication unit 110 may automatically end action of near-field wireless communication even though an operation end instruction is not accepted.

Moreover, for example, the operated equipment 101 may include a notification unit that notifies a user, with a sound, a screen display, or the like, of a fact that, when processing of the operated equipment 101 being relevant to an operation from the operation terminal 103 ends, a state where the sensor 106 detects that a container remains, for example, even after a predetermined time has elapsed, remains. Thereby, forgetting of taking of a container into which a beverage is poured, or the like can be prevented.

Moreover, for example, the example embodiment has been described with an example in which the operation terminal 103 has a function for operating the operated equipment 101, and the communication terminal 104 has a function for authenticating the operation.

However, the operation terminal 103 and the communication terminal 104 may be terminals each including both a function for operating the operated equipment 101 and a function for authenticating the operation.

Further, for example, the example embodiment has been described with an example in which an equipment code including an equipment ID is displayed by the equipment display unit 108, as an equipment code display means. However, the equipment code display means is not limited to a screen, and may be a surface of the operated equipment 101 having an equipment code printed thereon, a sticker having an equipment code printed thereon and being attached to the operated equipment 101, or the like.

Further, for example, the example embodiment has been described with an example in which the operation screen display unit 118 acquires operation screen information from the communication control apparatus 102 being an external apparatus.

However, the operation screen display unit 118 may acquire the operation screen information from the server apparatus 105 being another example of an external apparatus. Moreover, the operation terminal 103 may include an operation screen holding means for holding operation screen information being associated with an equipment ID, and the operation screen display unit 118 may acquire the operation screen information by use of the equipment ID from the operation screen holding means, instead of acquiring from an external apparatus. Such operation screen information may be included in, for example, a program module incorporated in the operation terminal 103.

Further, for example, the example embodiment has been described with an example in which transmission information includes operation history information, but the transmission information may include only communication history information without including the operation history information. Moreover, the terminal transmission unit 122 may transmit transmission information to an external apparatus, and the external apparatus may be one of the communication control apparatus 102 and the server apparatus 105, or may be an apparatus other than the communication control apparatus 102 and the server apparatus 105.

Further, for example, the present example embodiment has been described with an example in which the operation terminal 103 authenticates by acquiring an authentication ID from the communication terminal 104.

However, authentication processing may be able to authenticate that an operation of the operated equipment 101 is performed in presence of an authenticator.

For example, operation history information including an operation history at the operation terminal 103 may be held in each of the operation terminal 103 and the communication terminal 104. In this case, each of the operation terminal 103 and the communication terminal 104 may generate transmission information associating identification information of a counterpart terminal and a communication time of each other with the operation history information, and transmit the generated transmission information to one or both of the communication control apparatus 102 and the server apparatus 105.

Further, although a plurality of processes (pieces of processing) are described in order in a diagram illustrating a flow used in the above description, an execution order of the processes is not limited to the described order. An order of the processes may be changed to an extent that causes no problem in terms of content. Moreover, the one example embodiment and modified example described above may be combined to an extent that content does not contradict.

One means or all means according to the example embodiment described above can also be described as, but are not limited to, the following supplementary notes.

1. A communication control apparatus including:

a first wireless communication means for starting action of near-field wireless communication when acquiring a detection signal of a user or a target by a sensor installed in operated equipment or an apparatus relating to the operated equipment; and an operation means for operating the operated equipment by use of the first wireless communication means, based on information from the operation terminal.

2. The communication control apparatus according to supplementary note 1, wherein the operation means includes an acquisition means for acquiring, from the operation terminal, equipment information for identifying the operated equipment, and an output means for outputting, to the operation terminal, an operation screen of the operated equipment, based on the equipment information acquired by the acquisition means.

3. The communication control apparatus according to supplementary note 1 or 2, wherein the acquisition means acquires from the operation terminal that has acquired the equipment information included in a code.

4. The communication control apparatus according to any one of supplementary notes 1 to 3, wherein a code including the equipment information is output to a screen of the operated equipment, when action of near-field wireless communication is started.

5. The communication control apparatus according to any one of supplementary notes 1 to 4, wherein the first wireless communication means ends an operation of the near-field wireless communication, when an operation end instruction indicating ending of an operation of the operated equipment is accepted from the operation terminal, or when processing of the operated equipment being relevant to an operation from the operation terminal ends.

6. The communication control apparatus according to any one of supplementary notes 1 to 5, wherein the operated equipment is medical equipment, and the target is the operation terminal.

7. The communication control apparatus according to any one of supplementary notes 1 to 5, wherein the operated equipment is a vending machine in which a user stores a container, and the target is a container.

8. The communication control apparatus according to any one of supplementary notes 1 to 7, further including an operation history acquisition means for acquiring at least one of identification information of the operation terminal and identification information of the user, and the operation history, from the operation terminal via a second wireless communication means being different from the first wireless communication means.

9. The communication control apparatus according to any one of supplementary notes 1 to 8, further including a communication history acquisition means for acquiring information relating to a communication history between a communication terminal being different from the operation terminal and the operation terminal.

10. The communication control apparatus according to supplementary note 9, wherein the communication history includes identification information of the communication terminal, and a communication time between the communication terminal and the operation terminal.

11. An operation terminal including:

an equipment information acquisition means for acquiring equipment information for identifying operated equipment;

an operation screen acquisition means for acquiring operation screen information relating to an operation screen of the operated equipment, by use of the equipment information;

an output means for outputting the operation screen information acquired by the operation screen acquisition means;

an operation history storage means for storing an operation history via the operation screen; and an operation history transmission means for transmitting, to an external apparatus, transmission information including at least one of identification information of an operation terminal and identification information of a user, and the operation history.

12. The operation terminal according to supplementary note 11, wherein the operation screen acquisition means acquires the operation screen information from the external apparatus or an operation screen holding means for holding the operation screen information.

13. The operation terminal according to supplementary note 11, wherein the operation screen acquisition means acquires the operation screen information by use of the first wireless communication means, and the operation history transmission means transmits the transmission information by use of a second wireless communication means being different from the first wireless communication means.

14. The operation terminal according to any one of supplementary note 11 to 13, further including a communication history acquisition means for acquiring information relating to a communication history between a communication terminal being different from the operation terminal and the operation terminal, wherein the operation history transmission means includes the communication history in the transmission information instead of the operation history or together with the operation history.

15. The operation terminal according to supplementary note 14, wherein the communication history includes identification information of the communication terminal, and a communication time with the communication terminal.

16. An equipment operation system including:

a communication control apparatus and an operation terminal being capable of performing near-field wireless communication with each other, wherein the communication control apparatus includes a first wireless communication means for starting action of near-field wireless communication when acquiring a detection signal of a user or a target by a sensor installed in operated equipment or an apparatus relating to the operated equipment, and an operation means for operating the operated equipment by use of the first wireless communication means, based on information acquired from the operation terminal, and the operation terminal includes an equipment information acquisition means for acquiring equipment information for identifying the operated equipment, an operation screen display means for displaying an operation screen of the operated equipment, based on the equipment information, and an operation information transmission means for transmitting, to the first wireless communication means, the information according to an operation on the operation screen.

17. A communication control method including, by a computer:

starting action of near-field wireless communication when acquiring a detection signal of a user or a target by a sensor installed in operated equipment or an apparatus relating to the operated equipment; and operating the operated equipment by use of the near-field wireless communication, based on information from the operation terminal.

18. A program for causing a computer to execute:

starting action of near-field wireless communication when acquiring a detection signal of a user or a target by a sensor installed in operated equipment or an apparatus relating to the operated equipment; and operating the operated equipment by use of the near-field wireless communication, based on information from the operation terminal.

19. An operation terminal control method including, by a computer:

acquiring equipment information for identifying operated equipment;

acquiring operation screen information relating to an operation screen of the operated equipment, by use of the equipment information;

outputting the operation screen information acquired by the operation screen acquisition means; and transmitting, to an external apparatus, transmission information including at least one of identification information of an operation terminal and identification information of a user, and an operation history via the operation screen.

20. A program for causing a computer to execute:

acquiring equipment information for identifying operated equipment;

acquiring operation screen information relating to an operation screen of the operated equipment, by use of the equipment information;

outputting the operation screen information acquired by the operation screen acquisition means; and transmitting, to an external apparatus, transmission information including at least one of identification information of an operation terminal and identification information of a user, and an operation history via the operation screen.

REFERENCE SIGNS LIST

100 Equipment operation system
101 Operated equipment
102 Communication control apparatus
103 Operation terminal
104 Communication terminal
105 Server apparatus
106 Sensor
107 Activation instruction unit
108 Equipment display unit
109 Equipment control unit
110 First wireless communication unit
111 Operation unit
112 Second wireless communication unit
113 History acquisition unit
114 First equipment information acquisition unit
115 Output unit
116 Operation control unit
117 Second equipment information acquisition unit
118 Operation screen display unit
119 Operation acceptance unit
120 Operation history storage unit
121 Authentication unit
122 Terminal transmission unit

What is claimed is:

1. A communication control apparatus comprising:

at least one memory storing instructions; and at least one processor configured to execute the instructions to perform operations comprising:

starting action of near-field wireless communication that has been stopped, when acquiring a detection signal indicating that a user or a target is detected from a sensor for detecting the user or the target, the sensor being installed in operated equipment or an apparatus relating to the operated equipment; and operating the operated equipment by use of the near-field wireless communication, based on information from an operation terminal, wherein the target is different from the operation terminal, and operating the operated equipment includes acquiring, from the operation terminal, equipment information for identifying the operated equipment, and outputting, to the operation terminal, an operation screen of the operated equipment, based on the acquired equipment information.

2. The communication control apparatus according to claim 1, wherein acquiring equipment information includes acquiring the equipment information from the operation terminal that has acquired the equipment information included in a code.

3. The communication control apparatus according to claim 2, wherein a code including the equipment information is output to a screen of the operated equipment, when action of the near-field wireless communication is started.

4. The communication control apparatus according to claim 1, wherein an action of the near-field wireless communication is ended, when an operation end instruction indicating ending of an operation of the operated equipment is accepted from the operation terminal, or when processing of the operated equipment being relevant to an operation from the operation terminal ends.

5. The communication control apparatus according to claim 1, wherein the operated equipment is medical equipment.

6. The communication control apparatus according to claim 1, wherein the operated equipment is a vending machine in which the user stores a container, and the target is a container.

7. The communication control apparatus according to claim 1, further comprising acquiring at least one of identification information of the operation terminal and identification information of the user, and an operation history, from the operation terminal via a communication path being different from the near-field wireless communication.

8. The communication control apparatus according to claim 1, further comprising acquiring information relating to a communication history between a communication terminal being different from the operation terminal and the operation terminal.

9. The communication control apparatus according to claim 8, wherein the communication history includes identification information of the communication terminal, and a communication time between the communication terminal and the operation terminal.

10. An operation terminal comprising:

at least one memory storing instructions; and at least one processor configured to execute the instructions to perform operations comprising:

acquiring equipment information for identifying operated equipment;

acquiring operation screen information relating to an operation screen of the operated equipment, via first communication path by use of the equipment information;

outputting the acquired operation screen information;

storing an operation history via the operation screen; and transmitting, to an external apparatus via second communication path that is different communication path from the first communication path, transmission information including at least one of identification information of an operation terminal and identification information of a user, and the operation history, wherein the first communication path is a communication path using with near-field wireless communication that has been stopped and start when a user or a target is detected by a sensor for detecting the user or the target, the target is different from the operation terminal, and operating the operated equipment includes acquiring, from the operation terminal, equipment information for identifying the operated equipment, and outputting, to the operation terminal, an operation screen of the operated equipment, based on the acquired equipment information.

11. The operation terminal according to claim 10, wherein acquiring operation screen includes acquiring the operation screen information from the external apparatus or operation screen holding unit for holding the operation screen information.

12. The operation terminal according to claim 10, wherein acquiring the operation screen includes acquiring the operation screen information by use of a first communication path, and transmitting the transmission information includes transmitting the transmission information by use of a second communication path being different from the first communication path.

13. The operation terminal according to claim 10, further comprising acquiring information relating to a communication history between a communication terminal being different from the operation terminal and the operation terminal, wherein the transmission information includes the communication history instead of the operation history or together with the operation history.

14. The operation terminal according to claim 13, wherein the communication history includes identification information of the communication terminal, and a communication time with the communication terminal.

15. An equipment operation system comprising:

a communication control apparatus and an operation terminal being capable of performing near-field wireless communication with each other, wherein the communication control apparatus includes:

at least one memory storing instructions; and at least one processor configured to execute the instructions to perform operations including:

starting action of near-field wireless communication that has been stopped, when acquiring a detection signal indicating that a user or a target is detected from a sensor for detecting the user or the target, the sensor being installed in operated equipment or an apparatus relating to the operated equipment, and operating the operated equipment by use of the near-field wireless communication, based on information acquired from an operation terminal, and the target is different from the operation terminal, and the operation terminal includes:

at least one memory storing instructions; and at least one processor configured to execute the instruc-
tions to perform operations including:

acquiring equipment information for identifying the oper-
ated equipment, displaying an operation screen of the operated equipment,
based on the equipment information, and transmitting, to the communication control apparatus via
the near-field wireless communication, the information
according to an operation on the operation screen, and operating the operated equipment includes acquiring, from the operation terminal, equipment
information for identifying the operated equipment,
and outputting, to the operation terminal, an operation
screen of the operated equipment, based on the
acquired equipment information.

16. The communication control apparatus according to
claim 1, wherein the operated equipment and the commu-
nication control apparatus are physically separate appara-
tuses.

\* \* \* \* \*